United States Patent [19]

Hubball et al.

[11] Patent Number: 4,509,964

[45] Date of Patent: Apr. 9, 1985

[54] FUSED SILICA CAPILLARY COLUMN

[75] Inventors: John A. Hubball, Meriden, Conn.;
Eugene F. Barry, Nashua, N.H.

[73] Assignee: The Foxboro Company, Foxboro, Mass.

[21] Appl. No.: 568,074

[22] Filed: Jan. 4, 1984

[51] Int. Cl.³ .............................................. B01D 15/08
[52] U.S. Cl. ....................... 55/386; 65/30.1; 65/60.8; 210/198.2; 427/230
[58] Field of Search .................. 55/67, 386; 210/656, 210/198.2; 65/30.1, 60.8, 60.3; 427/36, 42, 230, 235, 299, 301

[56] References Cited

U.S. PATENT DOCUMENTS

| | | | |
|---|---|---|---|
| 4,045,353 | 8/1977 | Kosaka et al. | 55/386 |
| 4,293,415 | 10/1981 | Bente et al. | 55/386 |
| 4,376,641 | 3/1983 | Nestaick et al. | 55/386 |

Primary Examiner—John Adee
Attorney, Agent, or Firm—Parmelee, Bollinger, Bramblett & Drumm

[57] ABSTRACT

A gas chromatographic column comprising synthetic fused silica tubing irradiated in its raw state with gamma radiation of pre-selected dosage and dosage rate. The column further comprises a stationary phase coating of cyano-silicone immobilized and stabilized by cross-linking in situ by means of further irradiation by gamma radiation.

10 Claims, 1 Drawing Figure

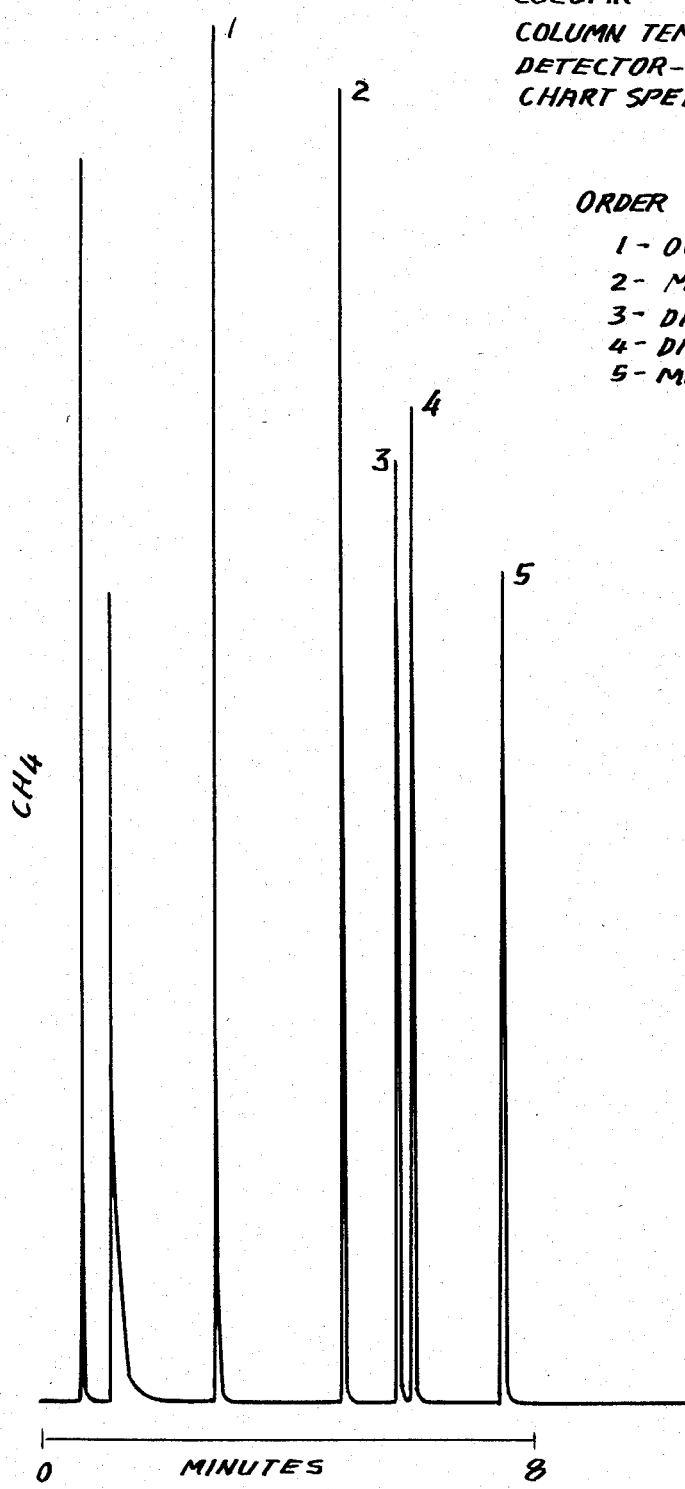

FUSED SILICA CAPILLARY COLUMN

BACKGROUND OF THE INVENTION

1. Field of the Invention

This invention relates to gas chromatography. More particularly, this invention relates to gas chromatography employing capillary columns, especially columns of fused silica.

2. Description of the Prior Art

Open tubular columns of capillary dimensions (i.e. less than 0.75 mm ID) are known to be capable of very high resolution. Although various column materials have been used, synthetic fused silica capillary columns have in recent years enjoyed considerable success due to important advantages, including toughness, flexibility and inertness.

The coatings applied to the inner wall of fused silica capillary columns (the so-called liquid phase or stationary phase) are categorized within a broad range extending from non-polar (little or no molecular interaction between the solutes and the liquid phase; that is, separation based on solute vapor pressure differences) to polar (separation based on the molecular interaction between the solutes and the liquid phase).

In order to take full advantage of fused silica capillary tubing, and to extend the range of capillary column applicability, it is necessary to employ fused silica capillary columns coated with polar liquid phases. Non-polar liquid phases offer no significant problems of application. However, the application of polar liquid phases to the inner wall of a fused silica capillary column has presented serious problems. For example, difficulty has been encountered due to the low wettability of a fused silica surface by most polar materials. That is, polar liquid phases tend to bead up on raw fused silica, resulting in an uneven coating with consequent poor performance. The deactivation of the raw fused silica also has presented additional problems.

Various proposals have been made for solving these problems. For example, a variety of surface modification procedures have been developed, including etching and leaching and the addition of different kinds of wetting agents. It now is commonly considered that a pre-coating should be applied to the inner wall of a fused silica column to aid in assuring that the final stationary phase coating can be applied smoothly, and meets other requirements of a chromatographic column. The material of such a pre-coating should be chemically related to that of the final coating in order to achieve good results. For example, if a final coating of cyano and methyl polysiloxane is to be used, a pre-coating of a compound including cyano might be applied first to assure that the final coating will be tightly bound to this pre-coat, evenly distributed, and effective in performance.

The use of such a pre-coating, or a pre-polymer, has not been a fully satisfactory solution to the problems discussed above. For example, satisfactory pre-coating materials are not available for all preferred stationary phases. Also, the pre-coating, when chemically different from the final coating, can interfere with the desired properties of the stationary phase, i.e. the pre-coating can "show through" the final coating and alter the selectivity. Moreover, the application of a pre-coating compound to the column inner wall is a relatively complex procedure, involving a number of closely-controlled steps which add significantly to the cost of producing a column, and make quality control difficult.

SUMMARY

In a preferred embodiment of the present invention, to be described hereinbelow in detail, the problems of applying a polar stationary phase to an open tubular column are substantially resolved by a pre-conditioning procedure wherein the inner surface of the column is subjected to gamma radiation prior to application of any coatings. Such radiation treatment is especially beneficial in increasing the wettability of fused silica by polar stationary phases. The radiation treatment also can advantageously serve to deactivate the column surface, providing a desirable combination of wettability and deactivation.

The mechanism by which gamma radiation treatment of raw fused silica produces these desired results is not now entirely understood. The radiation may be effective in part because it "roughs up" the surface of the inner wall of the column. It also is possible that the radiation, in developing additional silanol groups (SiOH), produces an increase in available energy for attracting the stationary phase molecules. Whatever the precise explanation, the resulting column has significantly improved characteristics, making it possible, for example, to eliminate the necessity of applying a pre-coating, or to enhance the capabilities of such pre-coating if used.

Accordingly, it is an object of this invention to provide an improved column for use in gas chromatography. Another object of this invention is to provide improved techniques for conditioning an open tubular chromatographic column to accommodate a polar stationary phase. Other objects, aspects and advantages of the invention are in part pointed out in, and in part apparent from, the following description of preferred embodiments of the invention, considered together with the accompanying drawing showing a chromatogram produced from a fused silica column conditioned in accordance with the present invention.

DESCRIPTION OF PREFERRED EMBODIMENTS

A chromatographic column formed in accordance with the present invention may comprise a fused silica capillary tube 15 meters in length, with an inner diameter of about 0.25 to 0.50 mm, and a wall thickness of about 0.02 mm. The column is provided in known fashion with a tough outer coating, e.g. a polyimide, to assure flexibility with relative freedom from fracture.

The stationary phase film on the inner wall of the column can be any of a number of commercially available preparations, such as the materials sold by General Electric Co. under the trade designations of XE-60 and XF-1150. Both of these are cyano-silicone stationary phases, comprising a combination of 2 cyano ethyl (usually referred to simply as "cyano") and methyl polysiloxane. In XE-60, the cyano is 25% of the total whereas in XF-1150, the cyano is 50% of the total. The cyano component provides polar characteristics in proportion to its concentration.

Prior to application of the stationary phase, the raw fused silica of the column is, in accordance with the invention, irradiated with gamma radiation from a suitable source. In one preferred embodiment, using a stationary phase film of XE-60, radiation was applied at an exposure rate of about 0.5 MRads/hour, for a period of 6 hours, to provide a total dosage of 3 MRads (megarads). The proper radiation treatment has however been found to depend upon the nature of the stationary phase material and upon characteristics of the fused silica. For XF-1150, on a commercially available fused silica, for example, it was found that the total dosage should be about 7 MRads, again applied at a rate of 0.5 MRads/hour.

The cyano-silicone stationary phases employed in the above examples preferably are further treated to effect immobilization (non-extractibility) and to provide thermal stability, as by known techniques of in situ cross-linking. In preferred embodiments of this invention, such immobilization and stabilization was effected by irradiating the stationary phase in situ with gamma radiation. In the case of the above column having a stationary phase of XE-60, a radiation exposure rate of 0.5 MRads/hour was applied for 24 hours, to provide a total dosage of 12 MRads for the coating. For a column coated with XF-1150, an exposure rate of 1.5 MRads was used to provide a total dosage of about 10 MRads.

For some applications, it may be beneficial to partially cross-link the stationary phase material by radiation applied to the liquid in bulk, prior to application to the column wall. This treatment can aid by increasing the viscosity of the polymer before coating the column, so as to produce a more gum-like substance having advantageous properties.

The single drawing FIGURE presents a chromatogram from a column constructed in accordance with the present invention. The column was fused silica 15 meters in length, irradiated as discussed above, and provided with an irradiated stationary phase film of XE-60 without any pre-coating. This column was operated at a temperature of 110° C., using a flame ionization detector (FID) operated at a sensitivity of $4 \times 10^{-11}$ ($1 \times 8$); the chart speed was 1.25 cm/minute.

The chromatogram shows excellent performance, demonstrating that the need for a pre-coating has been avoided by the initial gamma radiation treatment of the raw fused silica. The stationary phase was immobilized, and the resultant column exhibited excellent deactivation and efficiency which demonstrates good wettability and thus good film building qualities. Such a phase has excellent thermal stability, being capable for example of operating at temperatures as high as 240° C. without film deterioration.

The octanol peak in the chromatogram demonstrates good deactivation of the column. The nearly equal heights of the acidic solute (dimethylphenol) and the basic solute (dimethylaniline) show that the column advantageously has a neutral surface. That is, if there had been excess free silanol groups, there would be tailing and the dimethylaniline peak would be smaller.

The sequence of procedural steps for preparing a column in accordance with the invention typically would include a number of additional steps already well known and in use in the art. Thus, the raw fused silica tubing normally would first be purged with nitrogen to clear out such compounds as HCl which might be left over from the original fused-silica manufacturing process. After coiling the purged tubing to appropriate lengths, it is irradiated with gamma radiation at appropriate dosages as described above to promote wetting by the liquid phase, and to avoid the need for a conditioning layer. The column then is coated with the selected liquid phase and tested.

Thereafter, the coated column is further irradiated with gamma radiation at appropriate dosage and dosage rate to induce cross-linking of the liquid stationary phase. The column then may be rinsed with one or more suitable solvents. Such solvent might include methylene chloride and acetone. Rinsing with such a polar solvent mixture demonstrates that the film is well immobilized.

The rinsed column then is thermally conditioned. For example, the column temperature may be ramped up to an elevated temperature, e.g. at a ramp rate of 2 degrees/minute, and may be held during such conditioning at selected elevated temperatures for predetermined periods of time. Such thermal conditioning serves to drive off low-molecular weight material.

Thereafter, the column preferably is end-capped, using known techniques, to improve thermal stability. For example, a silizane compound may be sealed in the column for a period of time to react with and cover up active sites of the stationary phase. After final tests, the completed column may be shipped.

Although preferred embodiments of the present invention have been described herein in detail, it is desired to emphasize that this is for the purpose of illustrating the principles of the invention, and should not necessarily be construed as limiting the invention since it is apparent that those skilled in this art can make many modified arrangements of the invention without departing from the true scope thereof. For example, although the invention has been described specifically for use with polar stationary phases, it should be understood that it can advantageously be used with non-polar phases, e.g. by avoiding the need for deactivation with such phases.

What is claimed is:

1. The method of making a fused silica capillary column for use in gas chromatography comprising the steps of:
    irradiating fused silica capillary tubing with gamma radiation while the inner wall thereof is in a raw state, free from any coating; and thereafter
    applying a polar stationary phase coating to the inner wall of said tubing to form a chromatographic column.
2. The method of claim 1, wherein said stationary phase is a silicone compound.
3. The method of claim 2, wherein said stationary phase is cyano-containing.
4. The method of claim 1, wherein said stationary phase is stabilized by cross-linking.
5. The method of claim 4, wherein said cross-linking is effected by a further irradiation of said column with gamma radiation.
6. The method of claim 4, wherein said cross-linking is effected at least in part by irradiating the stationary phase material prior to its application to the column.
7. A chromatographic column produced in accordance with the process of claim 1.
8. A chromatographic capillary column of fused silica prepared by a process comprising the steps of:
    irradiating fused silica capillary tubing with gamma radiation while said fused silica is in a raw state, free of any coating; and thereafter
    applying a polar stationary phase coating to the inner wall of said tubing to form the chromatographic column.
9. The column of claim 8, wherein said stationary phase includes a silicone compound.
10. The column of claim 9, wherein said stationary phase includes cyano.

* * * * *